(12) United States Patent  
Krueger et al.

(10) Patent No.: US 7,291,382 B2  
(45) Date of Patent: Nov. 6, 2007

(54) LOW DENSITY FLEXIBLE RESILIENT ABSORBENT OPEN-CELL THERMOPLASTIC FOAM

(75) Inventors: Jeffrey Jennings Krueger, Marietta, GA (US); Renette E. Richard, Dunwoody, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 10/950,541

(22) Filed: Sep. 24, 2004

(65) Prior Publication Data

US 2006/0068187 A1    Mar. 30, 2006

(51) Int. Cl.  
*B32B 3/26* (2006.01)  
*B22C 1/22* (2006.01)  
*B29C 44/34* (2006.01)  
*C08F 14/00* (2006.01)  
*C08F 36/04* (2006.01)

(52) U.S. Cl. .................. 428/304.4; 521/139; 521/142; 521/146; 521/148

(58) Field of Classification Search .................. 517/79; 428/304.4, 308.4, 319.3, 319.7; 521/50, 521/139, 142, 146, 148  
See application file for complete search history.

(56) References Cited

U.S. PATENT DOCUMENTS

| | | | |
|---|---|---|---|
| 3,563,243 A | 2/1971 | Lindquist | |
| 3,911,922 A * | 10/1975 | Kliger | 604/362 |
| 4,076,673 A * | 2/1978 | Burkholder, Jr. | 524/389 |
| 4,142,956 A | 3/1979 | Shikinami et al. | |
| 4,229,396 A | 10/1980 | Suh et al. | |
| 4,279,848 A | 7/1981 | Baxter et al. | |
| 4,306,035 A | 12/1981 | Baskent et al. | |
| 4,318,408 A | 3/1982 | Korpman | |
| 4,329,052 A | 5/1982 | Colombo et al. | |
| 4,343,911 A | 8/1982 | Hoki et al. | |
| 4,384,032 A | 5/1983 | Tashiro et al. | |
| 4,394,930 A | 7/1983 | Korpman | |
| 4,415,388 A | 11/1983 | Korpman | |
| 4,423,110 A | 12/1983 | Sato | |
| 4,435,346 A | 3/1984 | Ito et al. | |
| 4,449,977 A | 5/1984 | Korpman | |
| 4,456,706 A * | 6/1984 | Siedenstrang et al. | 521/89 |
| 4,519,963 A | 5/1985 | Yoshida et al. | |
| 4,554,297 A | 11/1985 | Dabi | |
| 4,560,372 A | 12/1985 | Pieniak | |
| 4,579,872 A | 4/1986 | Johnson | |
| 4,655,210 A | 4/1987 | Edenbaum et al. | |
| 4,676,784 A | 6/1987 | Erdman et al. | |
| 4,725,629 A | 2/1988 | Garvey et al. | |
| 4,762,860 A | 8/1988 | Park | |
| 4,902,565 A | 2/1990 | Brook | |
| 5,116,662 A | 5/1992 | Morman | |
| 5,116,881 A | 5/1992 | Park et al. | |
| 5,132,171 A | 7/1992 | Yoshizawa et al. | |
| 5,133,917 A | 7/1992 | Jezic et al. | |
| 5,147,338 A | 9/1992 | Lang et al. | |
| 5,147,345 A | 9/1992 | Young et al. | |
| 5,158,986 A | 10/1992 | Cha et al. | |
| 5,180,751 A | 1/1993 | Park et al. | |
| 5,188,885 A | 2/1993 | Timmons et al. | |
| 5,203,764 A | 4/1993 | Libbey et al. | |
| 5,204,174 A | 4/1993 | Daponte et al. | |
| 5,210,138 A * | 5/1993 | Yamamoto et al. | 525/183 |
| 5,218,006 A | 6/1993 | Reedy et al. | |
| 5,250,577 A | 10/1993 | Welsh | |
| 5,268,224 A | 12/1993 | DesMarais et al. | |
| 5,269,987 A | 12/1993 | Reedy et al. | |
| 5,277,915 A | 1/1994 | Provonchee et al. | |
| 5,286,429 A | 2/1994 | Blythe et al. | |
| 5,290,822 A | 3/1994 | Rogers et al. | |
| 5,294,482 A | 3/1994 | Gessner | |
| 5,302,624 A | 4/1994 | Reedy et al. | |
| 5,318,735 A | 6/1994 | Kozulla | |
| 5,328,935 A | 7/1994 | Van Pahn et al. | |
| 5,331,015 A | 7/1994 | DesMarais et al. | |
| 5,342,857 A | 8/1994 | Reedy et al. | |
| 5,348,795 A | 9/1994 | Park | |
| 5,352,711 A | 10/1994 | DesMarais | |
| 5,356,944 A | 10/1994 | Blythe et al. | |
| 5,366,786 A | 11/1994 | Connor | |
| 5,387,207 A | 2/1995 | Dyer et al. | |
| 5,389,168 A | 2/1995 | Litchholt et al. | |
| 5,403,865 A | 4/1995 | Reedy et al. | |
| 5,405,883 A | 4/1995 | Park | |
| 5,411,687 A | 5/1995 | Imeokparia et al. | |
| 5,433,112 A | 7/1995 | Piche et al. | |
| 5,460,818 A | 10/1995 | Park et al. | |

(Continued)

FOREIGN PATENT DOCUMENTS

CA    2129278    2/1995

(Continued)

OTHER PUBLICATIONS

"Handbook of Plastic Foams", 1995, p. 308.*

(Continued)

*Primary Examiner*—Terrel Morris  
*Assistant Examiner*—Anish P. Desai  
(74) *Attorney, Agent, or Firm*—Pauley Petersen & Erickson

(57) ABSTRACT

A low density, flexible, resilient, absorbent open-cell thermoplastic foam includes a combination of thermoplastic elastomer, ethylene ionomer, stiff polymer, and surfactant selected to provide various advantageous properties. The foam is useful in personal care absorbent articles, medical absorbent articles, absorbent wiping articles, and a variety of other applications.

24 Claims, 1 Drawing Sheet

U.S. PATENT DOCUMENTS

| | | |
|---|---|---|
| 5,489,407 A | 2/1996 | Suh et al. |
| 5,496,864 A | 3/1996 | Henn et al. |
| 5,534,335 A | 7/1996 | Everhart et al. |
| 5,536,264 A | 7/1996 | Hsueh et al. |
| 5,536,563 A | 7/1996 | Shah et al. |
| 5,550,167 A | 8/1996 | DesMarais |
| 5,567,742 A | 10/1996 | Park |
| 5,573,994 A | 11/1996 | Kabra et al. |
| 5,585,411 A | 12/1996 | Hwo |
| 5,589,519 A | 12/1996 | Knaus |
| 5,595,694 A | 1/1997 | Reedy et al. |
| 5,618,853 A | 4/1997 | Vonken et al. |
| 5,646,194 A | 7/1997 | Kobayashi et al. |
| 5,674,916 A | 10/1997 | Schmidt et al. |
| 5,707,571 A | 1/1998 | Reedy |
| 5,728,406 A | 3/1998 | Halberstadt et al. |
| 5,744,506 A | 4/1998 | Goldman et al. |
| 5,763,067 A | 6/1998 | Brüggemann et al. |
| 5,767,189 A | 6/1998 | Palmer, Jr. |
| 5,770,634 A | 6/1998 | Dyer et al. |
| 5,788,889 A | 8/1998 | Demello et al. |
| 5,795,346 A | 8/1998 | Achter |
| 5,817,261 A | 10/1998 | Reedy et al. |
| 5,849,805 A | 12/1998 | Dyer |
| 5,855,572 A | 1/1999 | Schmidt |
| 5,880,166 A | 3/1999 | Glück et al. |
| 5,883,144 A | 3/1999 | Bambara et al. |
| 5,883,145 A | 3/1999 | Hurley et al. |
| 5,891,814 A | 4/1999 | Richeson et al. |
| 5,905,097 A | 5/1999 | Walther |
| 5,922,780 A | 7/1999 | Dyer et al. |
| 5,929,129 A | 7/1999 | Feichtinger |
| 5,962,545 A | 10/1999 | Chaudhary et al. |
| 5,993,706 A | 11/1999 | Wilkes et al. |
| 6,008,262 A | 12/1999 | McKay et al. |
| 6,017,832 A * | 1/2000 | Yahiaoui et al. ............ 442/118 |
| 6,027,795 A | 2/2000 | Kabra et al. |
| 6,030,696 A | 2/2000 | Lee |
| 6,051,174 A | 4/2000 | Park et al. |
| 6,071,580 A | 6/2000 | Bland et al. |
| 6,083,211 A | 7/2000 | DesMarais |
| 6,093,751 A | 7/2000 | Federico et al. |
| 6,093,752 A | 7/2000 | Park et al. |
| 6,096,793 A | 8/2000 | Lee et al. |
| 6,103,358 A | 8/2000 | Brüggemann et al. |
| 6,107,538 A | 8/2000 | Young et al. |
| 6,132,077 A | 10/2000 | Fogarty |
| 6,140,550 A | 10/2000 | Beihoffer et al. |
| 6,156,813 A | 12/2000 | Malwitz et al. |
| 6,174,471 B1 | 1/2001 | Park et al. |
| 6,197,233 B1 | 3/2001 | Mason et al. |
| 6,197,841 B1 | 3/2001 | Takimoto et al. |
| 6,221,928 B1 | 4/2001 | Kozma et al. |
| 6,231,960 B1 | 5/2001 | Dyer et al. |
| 6,235,360 B1 | 5/2001 | Lanzani et al. |
| 6,245,697 B1 | 6/2001 | Conrad et al. |
| 6,258,863 B1 | 7/2001 | Harfmann et al. |
| 6,258,868 B1 | 7/2001 | Heymann |
| 6,261,679 B1 | 7/2001 | Chen et al. |
| 6,262,137 B1 | 7/2001 | Kozma et al. |
| 6,262,138 B1 * | 7/2001 | Miyama et al. ............. 521/139 |
| 6,267,975 B1 * | 7/2001 | Smith et al. ................ 424/401 |
| 6,268,046 B1 | 7/2001 | Miller et al. |
| 6,281,289 B1 | 8/2001 | Maugans et al. |
| 6,297,326 B1 | 10/2001 | Wang et al. |
| 6,310,112 B1 | 10/2001 | Vo et al. |
| 6,325,956 B2 | 12/2001 | Chaudhary et al. |
| 6,329,450 B1 | 12/2001 | Ogoe et al. |
| 6,355,341 B1 | 3/2002 | Chaudhary et al. |
| 6,372,953 B1 | 4/2002 | Young et al. |
| 6,388,014 B1 | 5/2002 | Park et al. |
| 6,391,438 B1 | 5/2002 | Ramesh et al. |
| 6,398,997 B1 | 6/2002 | Ligon, Sr. et al. |
| 6,399,854 B1 | 6/2002 | Vartianen |
| 6,414,047 B1 | 7/2002 | Abe |
| 6,417,240 B1 | 7/2002 | Park |
| 6,436,521 B1 | 8/2002 | Lee |
| 6,451,865 B1 | 9/2002 | Migchels et al. |
| 6,458,877 B1 | 10/2002 | Ahmed et al. |
| 6,503,854 B1 * | 1/2003 | Abuto et al. ................. 442/149 |
| 6,653,360 B2 | 11/2003 | Gupta |
| 2002/0010270 A1 | 1/2002 | Czech et al. |
| 2002/0025988 A1 | 2/2002 | Maekawa et al. |
| 2002/0039869 A1 * | 4/2002 | Achille ....................... 442/417 |
| 2002/0137809 A1 * | 9/2002 | Kogure et al. ................ 521/79 |

FOREIGN PATENT DOCUMENTS

| | | |
|---|---|---|
| EP | 0 041 934 | 12/1981 |
| EP | 0 228 353 B1 | 5/1991 |
| EP | 0 328 518 B1 | 5/1991 |
| EP | 0 453 286 A2 | 10/1991 |
| EP | 0 475 174 B1 | 5/1996 |
| EP | 0 517 748 B1 | 12/1996 |
| EP | 0 642 907 B1 | 5/1997 |
| EP | 0 585 147 B1 | 4/1998 |
| EP | 0 878 481 A1 | 11/1998 |
| EP | 0 674 579 B1 | 6/2000 |
| EP | 0 662 493 B1 | 10/2000 |
| EP | 1 048 276 A1 | 11/2000 |
| EP | 1 115 777 B1 | 7/2001 |
| EP | 0 704 476 B1 | 12/2001 |
| EP | 1 182 224 A1 | 2/2002 |
| EP | 1 219 673 A2 | 7/2002 |
| EP | 1 219 673 A3 | 7/2002 |
| EP | 1 079 786 B1 | 8/2002 |
| EP | 0 702 032 B1 | 11/2002 |
| EP | 0 975 696 B1 | 6/2003 |
| GB | 2 259 464 A | 3/1993 |
| GB | 2 279 013 A | 12/1994 |
| JP | 4-46981 | 7/1992 |
| JP | 6-280317 | 10/1994 |
| JP | 2001-342277 | 12/2001 |
| WO | WO 86/00628 | 1/1986 |
| WO | WO 91/08037 | 6/1991 |
| WO | WO 94/13460 | 6/1994 |
| WO | WO 97/07907 | 3/1997 |
| WO | WO 97/11985 | 4/1997 |
| WO | WO 97/31053 | 8/1997 |
| WO | WO 98/10015 | 3/1998 |
| WO | WO 98/14508 | 4/1998 |
| WO | WO 98/16575 | 4/1998 |
| WO | WO 98/37131 | 8/1998 |
| WO | WO 98/41574 | 9/1998 |
| WO | WO 98/58991 | 12/1998 |
| WO | WO 99/00236 | 1/1999 |
| WO | WO 99/29765 | 6/1999 |
| WO | WO 99/47092 | 9/1999 |
| WO | WO 99/47592 | 9/1999 |
| WO | WO 99/52955 | 10/1999 |
| WO | WO 00/15697 | 3/2000 |
| WO | WO 00/15700 | 3/2000 |
| WO | WO 00/53669 | 3/2000 |
| WO | WO 01/09239 A1 | 2/2001 |
| WO | WO 01/15643 A1 | 3/2001 |
| WO | WO 01/16220 A1 | 3/2001 |
| WO | WO 01/21227 A1 | 3/2001 |
| WO | WO 01/27191 A1 | 4/2001 |
| WO | WO 01/34687 A1 | 5/2001 |
| WO | WO 01/40374 A2 | 6/2001 |
| WO | WO 01/40374 A3 | 6/2001 |
| WO | WO 01/64154 A1 | 9/2001 |
| WO | WO 01/70479 A1 | 9/2001 |
| WO | WO 01/70859 A2 | 9/2001 |

| WO | WO 01/70859 A3 | 9/2001 |
| WO | WO 01/70860 A2 | 9/2001 |
| WO | WO 01/70860 A3 | 9/2001 |
| WO | WO 01/80916 A2 | 11/2001 |
| WO | WO 01/80916 A3 | 11/2001 |
| WO | WO 02/07791 A2 | 1/2002 |
| WO | WO 02/07791 A3 | 1/2002 |
| WO | WO 02/12379 A1 | 2/2002 |
| WO | WO 02/14424 A2 | 2/2002 |
| WO | WO 02/18482 A2 | 3/2002 |
| WO | WO 02/22339 A1 | 3/2002 |
| WO | WO 02/34823 A2 | 5/2002 |
| WO | WO 02/068530 A2 | 9/2002 |
| WO | WO 2005/061600 A1 | 7/2005 |

OTHER PUBLICATIONS

Rynel EPITECH® brochure, 1997.

Jeffrey Csemica and Alisha Brown, "Effect of Plasticizers on the Properties of Polystyrene Films", Journal of Chemical Education, vol. 76, No. 11, Nov. 1999, pp. 1526-1528.

"Kraton D and G Polymers," www.Kraton.com/kraton/generic/menu.asp?ID=220, Oct. 2001.

Epolene® Polymers brochure, Eastman Chemical Company, 2002, pp. 9, 11, 12.

"Epolene Polymers", www.eastman.com/Brands/Epolene/Epolene_Intro.asp, 2003.

"Epolene Polymers," www.eastman.com/Online_Publications/F243/f24304.htm, 1994.

Principles of Polymer Systems, Ferdinand Rodriguez, McGraw-Hill Book Co., 1070, pp. 43-46, Apr. 1996.

* cited by examiner

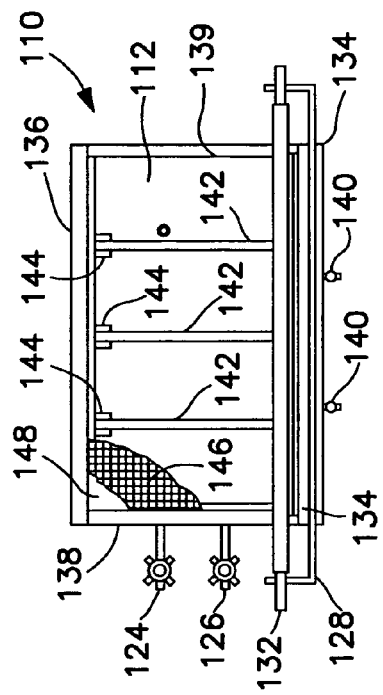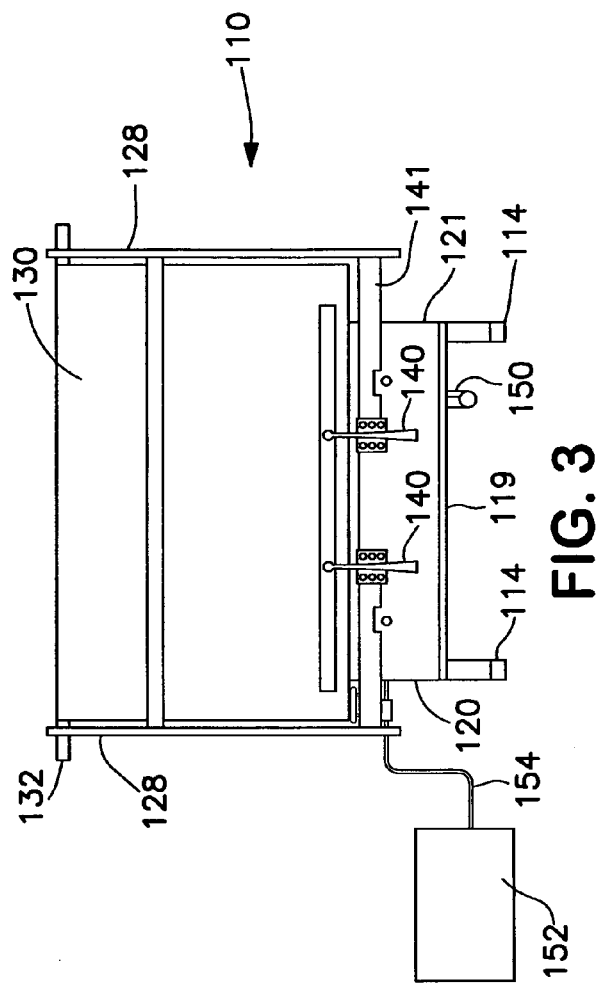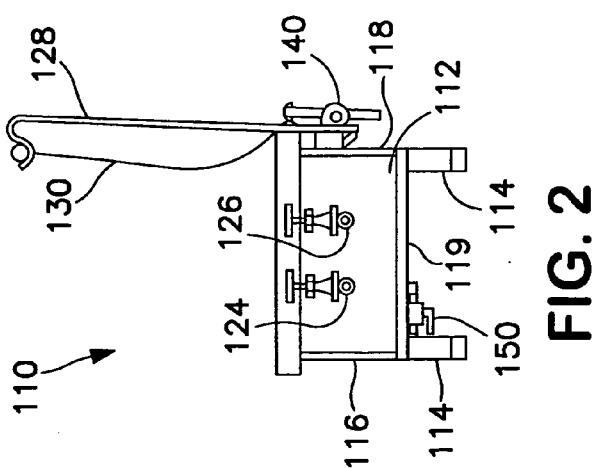

LOW DENSITY FLEXIBLE RESILIENT ABSORBENT OPEN-CELL THERMOPLASTIC FOAM

BACKGROUND OF THE INVENTION

This invention is directed to a low density absorbent open-cell thermoplastic foam that is flexible and resilient. The foam is useful to produce a wide variety of personal care, health and medical care products.

Previous attempts to foam thermoplastic materials using thermoplastic elastomer, such as styrene block copolymer, often have not yielded low density open-celled materials. The properties of low density have been enhanced using a crosslinking agent which crosslinks the materials during extrusion. The crosslinking substantially hardens the foam and requires additional processing skills. Also, the possible existence of residual crosslinking agent makes this process less desirable for foams used in personal care, health and medical care products, which contact the human skin.

PCT International Publication WO 02/18482 discloses a thick extruded open-cell foam formed of a composition consisting of 4.5-75 parts by weight ethylene ionomer resin, 0.5-3.0 parts by weight polyolefin resin having a melting point exceeding 120° C., and 20-95 parts by weight of one or more polymers selected from the group of ethylene-propylene rubbers, styrene elastomers and polyethylene resins having a melting point of 120° C. or lower, wherein the foregoing polymers add up to 100 parts by weight. The foam is useful for packaging material, bags, fruit trays and other containers, and has shock absorption properties. While the described foam has flexibility, it possesses enough rigidity for these applications. Also, while the described foam may absorb some water, due to its open-cell structure, water absorption is not a primary function.

There is a need or desire for a low density, flexible, resilient, absorbent open-cell thermoplastic foam suitable for use in personal care, health and medical care products, many of which require softness and absorbency as primary features.

SUMMARY OF THE INVENTION

The present invention is directed to a low density, flexible, resilient, absorbent open-cell thermoplastic foam suitable for use in personal care, health and medical care products. The invention is also directed to personal care, health and medical care products containing the foam.

The foam of the invention includes a foam formula having the following ingredients:
A) about 5 to about 70 parts by weight thermoplastic elastomer selected from the group consisting of styrenic block copolymers, olefin elastomers and combinations thereof;
B) about 5 to about 70 parts by weight ethylene ionomer;
C) about 15 to about 60 parts by weight of a stiff polymer selected from the group consisting of polystyrene, high impact polystyrene, high density polyethylene, linear low density polyethylene, low density polyethylene, polypropylene and combinations thereof; and
D) about 0.05 to about 5 parts by weight surfactant effective for increasing the wettability of the foam cells;
wherein the sum of A, B, C and D equals 100 parts by weight.

The thermoplastic elastomer contributes softness, flexibility and resiliency to the foam, and improves its structural integrity, including enhanced resistance to abrasion and fracture. The ethylene ionomer contributes to flexibility and the stabilization of cells during cell formation. The stiff polymer contributes to dimensional stability and processing of the foam. The surfactant renders the foam wettable, enhances its absorbent capability, and helps stabilize the foam cells during cell formation.

The foam adds comfort, absorbency and durability to personal care, health and medical products as described below. The foam remains absorbent after repeated washing and use of the article.

With the foregoing in mind, it is a feature and advantage of the invention to provide an improved open-celled thermoplastic absorbent foam, and articles containing it.

BRIEF DESCRIPTION OF THE DRAWINGS

FIG. 1 is a partially cut away representative top view of a saturated capacity tester.

FIG. 2 is a representative side view of a saturated capacity tester for measuring absorbent capacity as described below.

FIG. 3 is a representative rear view of a saturated capacity tester.

DEFINITIONS

"Absorbent" refers to a foam capable of absorbing at least 100% of its own weight of aqueous sodium chloride solution (0.9% by weight NaCl) using the saturated capacity test described below.

"Absorbent article" includes, but is not limited to, personal care absorbent articles, medical absorbent articles, absorbent wiping articles, as well as non-personal care absorbent articles including filters, masks, packaging absorbents, trash bags, stain removers, topical compositions, laundry soil/ink absorbers, detergent agglomerators, lipophilic fluid separators, cleaning devices, and the like.

"Absorbent wiping article" includes facial tissue, towels such as kitchen towels, disposable cutting sheets, away-from-home towels and wipers, wet-wipes, sponges, washcloths, bath tissue, and the like.

"Cell" refers to a cavity contained in foam. A cell is closed when the cell membrane surrounding the cavity or enclosed opening is not perforated and has all membranes intact. Cell connectivity occurs when at least one wall of the cell membrane surrounding the cavity has orifices or pores that connect to adjacent cells, such that an exchange of fluid is possible between adjacent cells.

"Compression" refers to the process or result of pressing by applying force on an object, thereby increasing the density of the object.

"Elastomer" refers to material having elastomeric or rubbery properties. Elastomeric materials, such as thermoplastic elastomers, are generally capable of recovering their shape after deformation when the deforming force is removed. Specifically, as used herein, elastomeric is meant to be that property of any material which upon application of an elongating force, permits that material to be stretchable to a stretched length which is at least about 50 percent greater than its relaxed length, and that will cause the material to recover at least 50 percent of its elongation upon release of the stretching elongating force. A hypothetical example which would satisfy this definition of an elastomeric material in the X-Y planar dimensions would be a one (1) inch sample of a material which is elongatable to at least 1.50 inches and which, upon being elongated to 1.50 inches and released, will recover to a length of not more than 1.25 inches. Many elastomeric materials may be stretched by much more than 50 percent of their relaxed length, and many of these will recover to substantially their original relaxed length upon release of the stretching, elongating force. In addition to a material being elastomeric in the described X-Y planar dimensions of a structure, including a web or sheet, the material can be elastomeric in the Z planar dimension. Specifically, when a structure is applied compression, it displays elastomeric properties and will essentially recover to its original position upon relaxation. Compression set is sometimes used to describe such elastic recovery.

"Medical absorbent article" includes a variety of professional and consumer health-care products including, but not limited to, products for applying hot or cold therapy, hospital gowns, surgical drapes, bandages, wound dressings, covers, containers, filters, disposable garments and bed pads, medical absorbent garments, gowns, underpads, wipes, and the like.

"Menses simulant" is a material that simulates the viscoelastic and other properties of menses, which is a "complex liquid." As used herein, the phrase "menses simulant" or "complex liquid" describes a liquid generally characterized as being a viscoelastic fluid comprising multiple components having inhomogeneous physical and/or chemical properties. It is the inhomogeneous properties of the multiple components that challenge the efficacy of an absorbent or adsorbent material in the handling of complex liquids. In contrast with complex liquids, simple liquids, such as, for example, urine, physiological saline, water, and the like, are generally characterized as having a relatively low viscosity and comprising one or more components having homogeneous physical and/or chemical properties. As a result of having homogeneous properties, the one or more components of simple liquids behave substantially similarly during absorption or adsorption, although some components may be absorbed or adsorbed more readily than others. Although a complex liquid is generally characterized herein as including specific components having inhomogeneous properties, each specific component of a complex liquid generally has homogeneous properties. Consider for example a representative complex body-liquid having three specific components: red blood cells, blood protein molecules, and water molecules. Upon examination, one skilled in the art could easily distinguish between each of the three specific components according to their generally inhomogeneous properties. Moreover, when examining a particular specific component, such as the red blood cell component, one skilled in the art could easily recognize the generally homogeneous properties of the red blood cells. The "menses simulant" test fluid used in this invention is composed of swine blood diluted with swine plasma to provide a hematocrit level of 35% (by volume). A suitable device for determining the hematocrit level is a HEMATOSTAT-2 system, available from Separation Technology, Inc., a business having offices located in Altamonte Springs, Fla., U.S.A. A substantially equivalent system may alternatively be employed.

"Open-cell" refers to any cell that has at least one broken or missing membrane or a hole in a membrane.

"Open-celled foam" refers to a foam including a multiplicity of cells, having an open-cell content of at least about 50%, measured using ASTM D2856, Method C.

"Personal care absorbent article" includes, but is not limited to, absorbent articles such as disposable diapers, baby wipes, training pants, child-care pants, and other disposable garments; feminine-care products including sanitary napkins, wipes, menstrual pads, panty liners, panty shields, interlabials, tampons, and tampon applicators; adult-care products including wipes, pads, containers, incontinence products, and urinary shields; and the like.

"Plasticizing agent" refers to a chemical agent that can be added to a rigid polymer to add flexibility to rigid polymers. Plasticizing agents typically lower the glass transition temperature.

"Polymer" generally includes but is not limited to, homopolymers, copolymers, including block, graft, random and alternating copolymers, terpolymers, etc., and blends and modifications thereof. Furthermore, unless otherwise specifically limited, the term "polymer" shall include all possible molecular geometrical configurations of the material. These configurations include, but are not limited to isotactic, syndiotactic and atactic symmetries.

"Stiff polymer" refers to polymers that are inelastic, i.e., polymers that are not "elastic" as defined above.

"Surfactant" is a compound, such as detergents and wetting agents, that affects the surface tension of fluids.

"Thermoplastic" is meant to describe a material that softens and/or flows when exposed to heat and which substantially returns to its original hardened condition when cooled to room temperature.

"Viscous fluid" refers to a fluid having a viscosity greater than the viscosity of water, including such fluids as menses, menses simulant, fecal fluid, fecal fluid simulant, and the like.

DESCRIPTION OF THE PREFERRED EMBODIMENTS

The foam of the invention is a low density, flexible, resilient, absorbent open-cell thermoplastic foam. The foam has a density of about 225 kilograms/cubic meter ($kg/m^3$) or less, suitably about 175 $kg/m^3$ or less, particularly about 125 $kg/m^3$ or less, before any compression is applied. The foam has a flexibility characterized by a buckling (bending) pressure of about 500 kilopascals (kPa) or less, suitably about 250 kPa or less, particularly about 100 kPa or less, measured using the Edge Compression Test Method described below.

The foam has an absorbency of at least about one gram aqueous liquid (0.9% by weight NaCl) per gram of dry foam, suitably at least about two grams aqueous liquid per gram of dry foam, particularly at least about three grams of aqueous liquid per gram of dry foam, measured using the Saturated Capacity Test described below. The foam has a fluid intake rating of about 5 to about 9, suitably about 7 to about 9, using the Fluid Intake Rating Test. The foam has a vertical wicking height of at least about 3.5 cm, suitably at least about 4.5 cm, particularly at least about 5.5 cm, using the Vertical Wicking Test Method.

The foam has an open-cell content of at least about 60%, suitably at least about 70%, particularly at least about 80%, measured using ASTM D2856, Method C. The open-cell content, and the type and amount of surfactant employed, influence the absorbent characteristics of the foam.

The foam includes 100 parts by weight of a foam formula. The foam formula includes A) about 5 to about 70 parts by weight thermoplastic elastomer, B) about 5 to about 70 parts by weight ethylene ionomer, C) about 15 to about 60 parts by weight stiff polymer, and D) about 0.5 to about 5 parts by weight surfactant. The foam formula may include about 10 to about 50 parts by weight thermoplastic elastomer, about 10 to about 50 parts by weight ethylene ionomer, about 25 to about 60 parts by weight stiff polymer, and about 1 to about 4 parts by weight surfactant. In particular, the foam formula may include about 20 to about 40 parts by weight thermoplastic elastomer, about 15 to about 40 parts by weight ethylene ionomer, about 35 to about 60 parts by weight stiff polymer and about 1.5 to about 4 parts by weight surfactant. The sum of A, B, C and D equals 100 parts by weight.

The thermoplastic elastomer A is suitably selected from the group consisting of styrenic block copolymer, olefin elastomers, and combinations thereof. Styrene block copolymer elastomers include without limitation diblock copolymers, triblock copolymers, tetrablock copolymers and combinations thereof. Styrene diblock copolymers include without limitation styrene-butadiene, styrene-isoprene, styrene-(ethylene-butylene) which can be formed by selective hydrogenation of the butadiene units in styrene-butadiene, and styrene-(ethylene-propylene) which can be formed by selective hydrogenation of the isoprene units in styrene-isoprene. Styrene triblock copolymers include without limitation styrene-butadiene-styrene, styrene-isoprene-styrene, styrene-(ethylene-butylene)-styrene which can be formed by selective hydrogenation of styrene-butadiene-styrene, and styrene-(ethylene-propylene)-styrene which can be formed by selective hydrogenation of styrene-isoprene-styrene. Styrene tetrablock copolymers include without limitation styrene-butadiene-styrene-butadiene, styrene-isoprene-styrene-isoprene, styrene-(ethylene-butylene)-styrene-(ethylene-butylene), and styrene-(ethylene-propylene)-styrene-(ethylene-propylene).

Suitable styrene block copolymers are commercially available from Kraton Polymers LLC of Belpre, Ohio under the trade name KRATON®; from Dexco (division of Exxon-Mobil Chemical Co.) of Houston, Tex. under the trade name VECTOR®; and from Kuraray America, Inc. of New York, N.Y., under the trade name SEPTON®. In one suitable embodiment, the thermoplastic elastomer A) is selected from the group consisting of styrene block copolymers and combinations thereof.

Olefin elastomers include without limitation ethylene-propylene rubber (EPR), which is a random or block copolymer containing about 20-80% by weight ethylene and about 20-80% by weight propylene. Other olefin polymers include ethylene-propylene-diene polymers, ethylene vinyl acetate, ethylene methyl acrylate, and stereoblock polypropylenes. Also included are single-site catalyzed ethylene polymers and ethylene-alpha olefin copolymers having a density less than about 0.89 grams/cm$^3$, such as those available from Dow Chemical Co. in Midland, Mich. under the trade name AFFINTY™.

The thermoplastic elastomer A may also be, or may include, dynamic vulcanized elastomer-thermoplastic blends; thermoplastic polyether ester elastomers; ionomeric thermoplastic elastomers; thermoplastic elastic polyurethanes, including those available from E.I. Du Pont de Nemours in Wilmington, Del., U.S.A., under the trade name LYCRA® polyurethane, and ESTANE® available from Noveon, Inc. in Cleveland, Ohio, U.S.A.; thermoplastic elastic polyamides, including polyether block amides available from ATOFINA Chemicals, Inc. in Philadelphia, Pa., U.S.A., under the trade name PEBAX® polyether block amide; thermoplastic elastic polyesters, including those available from E.I. Du Pont de Nemours Company, under the trade name HYTREL®, and ARNITEL® from DSM Engineering Plastics of Evansville, Ind., U.S.A.

The ethylene ionomer is suitably a polymer having the following chemical structure:

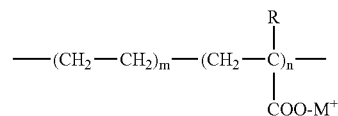

where M is sodium, potassium, lithium, magnesium, zinc or strontium,
R is hydrogen or an alkyl group having 1 to 6 carbon atoms,
m and n are integers, and
the ratio of m/n is about 10 to about 100.

Suitable ethylene ionomers include without limitation thermoplastic ionomers based on ethylene acrylic acid, ethylene methacrylic acid, other ethylene alkylacrylic acid copolymers, and ethylene alkyl acrylate copolymers. The percent neutralization is the percentage of carboxylic acid linkages that are neutralized with a metal salt. The percent neutralization may range from about 5 to about 100%, and is suitably about 8 to about 85%, particularly about 10 to about 70% When the metal ion has a valence of two, such as zinc, one metal ion may neutralize two polymer molecules and link them together. Suitable thermoplastic ionomers are available from E.I. DuPont DeNemours & Co. under the trade name SURLYN®.

The stiff polymer is selected from the group consisting of polystyrene, high impact polystyrene, high density polyethylene, linear low density polyethylene, low density polyethylene, polypropylene and combinations thereof. Suitably, the stiff polymer is selected from the group consisting of polystyrene, high impact polystyrene, and combinations thereof. Suitably polystyrene resins may have a melt flow rate of about 1.5 to about 15 grams/10 min. measured using ASTM D1238, condition G; a Vicat softening temperature of about 88-115° C. measured using ASTM D1525; a weight average molecular weight of about 95,000 to about 300,000; and a number average molecular weight of about 70,000 to about 130,000. One suitable polystyrene resin is STYRON® 685D, available from Dow Chemical Co. in Midland, Mich.

High impact polystyrene (HIPS) is polystyrene modified with small amounts of rubber. Rubber is dissolved in the monomer feed stream used to form polystyrene. Polymerization can then be carried out in an agitated tower-type reactor or another suitable reactor. The resulting polystyrene product contains small rubber domains that contribute significant toughness to the product. Some of the rubber is grafted onto the polystyrene. Suitable rubber materials include without limitation polybutadiene, styrene butadiene copolymers, ethylene-propylene elastomers, and ethylene-propylene-diene elastomers.

High density polyethylene is polyethylene having a density of about 0.940-0.965 grams/cm$^3$, a melting point of about 125-132° C., and a highly linear chain structure or a low degree of branching (i.e., up to three methyl branches per 1000 carbon atoms). High density polyethylene is produced using a conventional low pressure, slurry phase polymerization process, and can be made using a Ziegler-Natta catalyst, a single-site (e.g., metallocene) catalyst, or another suitable catalyst. Suitable high density polyethylenes have a melt index of about 1.0-15 grams/10 min. measured at 190° C. using ASTM D1238.

Linear low density polyethylene is typically a random copolymer of ethylene with an alpha-olefin comonomer having 3-20 carbon atoms. Linear low density polyethylene may have a density of about 0.910 to less than 0.940 grams/cm$^3$, a melting point of about 100-125° C., and a highly linear chain structure or a low degree of branching, similar to high density polyethylene. The density and melting point are affected by the type and amount of alpha-olefin comonomer, with heavier comonomers and/or higher amounts leading to lower densities and melting points. Typical linear low density polyethylenes contain a butene, hexene, or octene comonomer, in amounts of about 2-15% by weight. Linear low density polyethylene can be made using the same processes and catalysts as high density polyethylene. Suitable linear low density polyethylenes have a melt index of about 1.0-15 grams/10 min. measured at 190° C. using ASTM D1238.

Low density polyethylene is typically an ethylene homopolymer having a density of about 0.910 to less than about 0.940 grams/cm$^3$, a melting point of about 100-120° C., and a high level of short chain branches (e.g., 15-25 methyl branches per 1000 carbon atoms). Low density polyethylene is typically produced using a conventional high pressure free-radical polymerization process using a Ziegler-Natta catalyst, a single-site catalyst, or another suitable catalyst. Suitable low density polyethylenes have a melt index of about 1.0-15 grams/10 min., measured at 190° C. using ASTM D1238.

Polypropylene polymers suitable for use as the stiff polymer include propylene homopolymers and propylene-ethylene copolymers containing up to about 10% by weight ethylene. Suitable polypropylenes have a density of about 0.89 to about 0.93 grams/cm$^3$, a melting point of about 135-165° C., and a melt flow rate of about 0.4-40 grams/10 min., measured at 230° C. using ASTM D1238. Polypropylenes may be produced by any conventional process using a Ziegler-Natta catalyst, a single site catalyst, or another suitable catalyst.

The surfactant component of the foam formula enhances the uniformity of cell distribution within the thermoplastic foam, and enhances its absorbency by producing a wettable and/or hydrophilic surface for the transfer of aqueous liquids within the foam. The surfactant component can include one or more surfactants. The surfactant component should be thermally stable at foam processing conditions, typically up to about 200° C. Also, the surfactant should be sufficiently mobile in the molten foam composition to properly orient on the surface of the thermoplastic foam. Also, the surfactant should have a suitable molecular architecture for the desired foam properties. The surfactant molecular weight should be large enough to provide optimum wetting, yet not so large as to increase the cell dimensions in the thermoplastic foam to undesired levels. Branched polymer surfactants form larger cells than linear polymer surfactants.

Suitable surfactants include without limitation ethoxylated dimethylsiloxane surfactants, polyoxyethylene copolymer surfactants, block copolymers of ethylene oxide and propylene oxide, organic sulfates, organic sulfonates, alkyl polyglycosides, polyolefin glycol derivatives, and combinations thereof. Examples include the following:

Ethoxylated Dimethylsiloxane Surfactants

1. MASIL® SF-19, available from BASF Corporation, is a low molecular weight surfactant useful in combination with HS-1 or TWEEN® (described below).

2. MMF-184SW, available from Siltech, is a medium molecular weight surfactant useful in combination with HS-1 (described below).

3. Dow Corning 193 Fluid, available from Dow Corning Co., is a high molecular weight surfactant which forms relatively large foam cells.

Polyoxyethylene Copolymer Surfactants

1. TWEEN® 40, available from Uniqema Chemical Co., based on polyoxyethylene 20 sorbitan monopalmitate, is useful for producing fine celled foams but (by itself) does not enhance wettability.

2. TWEEN® 60, available from Uniqema Chemical Co., based on polyoxyethylene 20 sorbitan monostearate, is wettable and useful for forming medium-sized foam cells.

3. TWEEN® 80, available from Uniqema Chemical Co., based on polyoxyethylene 20 sorbitan monooleate, is not wettable and should be combined with a surfactant that enhances wettability.

Block Copolymers of Ethylene Oxide and Propylene Oxide

1. PLURONIC® F38, available from BASF Corp., is a hydrophilic surfactant based on small molecules, and may be combined with HS-1 (described below).

2. PLURONIC® F98, available from BASF Corp., is a hydrophilic surfactant based on large molecules.

3. PLURONIC® L43, available from BASF, is less hydrophilic, based on small molecules, and may be combined with HS-1 (described below).

4. PLURONIC® L92, available from BASF, is less hydrophilic, based on large molecules, and may be combined with HS-1 (described below).

Organic Sulfate and Sulfonate Surfactants

1. WITCONATE® AOK, available from Akzo Nobel Co., based on sodium alkyl sulfonate containing 14-16 carbon atoms per molecule, is marginally effective.

2. WITCONATE® K Dense, available from Akzo Nobel Co., based on sodium dodecylbenzene sulfonate, is very effective.

3. WITCONATE® NAS-8, available from Akzo Nobel Co., based on sodium octane sulfonate, is useful when combined with HS-1 (described below).

4. WITCONATE® P-1059, available from Akzo Nobel Co., based on amine alkylbenzenesulfonate, is wettable yet produces somewhat stiffer foams.

5. WITCONATE® AOS-12, available from Akzo Nobel Co., based on sodium alpha-olefin sulfonate, may be effective.

6. WITCONATE® 1050, available from Akzo Nobel Co., based on sodium alkyl pareth sulfonate having 12-15 carbon atoms, may be effective.

7. WITCONATE® DS Dense, available from Akzo Nobel Co., based on linear sodium alkylbenzene sulfonate, may be effective.

8. WITCONATE® LES-60C, available from Akzo Nobel Co., based on sodium lauryl ether sulfate, may be effective.

9. HOSTASTAT® HS-1, available from Clariant Corp., based on alkylsulfonate having 8-16 carbon atoms, is effective in forming fine foam cells.

Alkyl Polyglycoside

GLUCOPON® 220 USP, available from Henkel Corp., based on alkyl polyglycoside, forms fine cells in foam.

Polyethylene Glycol Derivatives

1. EMEREST® 2650, available from Cognis Corp., based on polyethylene glycol 400 monolaurate, is not wettable and forms relatively large foam cells.

2. EMEREST® 2648, available from Cognis Corp., based on polyethylene glycol 400 dioleate, is not wettable and forms large foam cells.

3. EMEREST® 2712, available from Cognis Corp., based on polyethylene glycol 400 distearate, is not wettable and should be combined with a wettable surfactant.

The thermoplastic foam of the invention includes at least about 50% by weight of the above-described foam formula, suitably at least about 75% by weight, particularly at least about 85% by weight. In addition to the above-described foam formula, the thermoplastic foam may include blowing agents, nucleating agents, cell stabilizers, antistatic agents, pigments, and other conventional ingredients.

Blowing agents include physical and chemical blowing agents, and may be inorganic or organic. Inorganic blowing agents include water, nitrogen, carbon dioxide, air, argon and helium. Organic blowing agents include hydrocarbons such as methane, ethane, propane, butanes, pentanes, hexanes, and the like. Aliphatic alcohols and halogenated hydrocarbons, including FREON® and HFC-134A, can also be used though in the latter, their use is generally avoided for environmental reasons. Endothermic and exothermic chemical blowing agents which are typically added at the extruder hopper include: azodicarbonamide, paratoluene sulfonyl hydrazide, azodiisobutyro-nitrile, benzene sulfonyl hydrazide, P-toluene sulfonyl hydrazide, barium azodicarboxylate, sodium bicarbonate, sodium carbonate, ammonium carbonate, citric acid, toluene solfonyl semicarbazide, dinitroso-pentamethylene-tetramine, phenyltetrazole sodium borohydride, and the like. Mixtures and combinations of various physical and chemical blowing agents can be used and often are used to control cell structure. Blowing agent activators can be added to lower the decomposition temperature/profile of such chemical blowing agents. Such activators include metals in the form of salts, oxides, or organometallic complexes. Blowing agents may constitute about 1-10% by weight of the thermoplastic foam.

Nucleating agents can be employed to obtain desired fine open-cell structure. The amount of nucleating agent will vary according to the cell structure desired, foaming temperature, pressure, polymer composition, and type of nucleating agent utilized. Typically with increasing nucleating agent, cell density and open-cell content increase. Nucleating agents include calcium carbonate, blends of citric acid and sodium bicarbonate, coated citric acid/sodium bicarbonate particles, nanoclays, silica, barium stearate, diatomaceous earth, titanium dioxide, talc, pulverized wood, clay, and calcium stearate. Stearic acid, salicylic acid, fatty acids, and metal oxides can also be used as foaming aids. Other thermoplastic polymers can also be used for such purposes. These are typically dry blended or added with the polymer concentrate. One suitable nucleating agent is Luzenac MISTRON® Vapor talc, available from Luzenac America, located in Centennial, Colo. Another nucleating agent is CLOISTE® ZOA nanoclay, available from Southern Clay Products, Inc., in Gonzales, Tex. Nucleating agents may constitute about 0.1-5% by weight of the thermoplastic foam.

Open-cell formation can be regulated by elevated processing pressures and/or temperatures and use of nucleating agents and chemical blowing agents which can control both cell density and cell structure. Various base resins are sometimes used to broaden the foaming temperature to make open-cell foam. Open-cell level can be facilitated by adding small amounts of various immiscible polymers to the foam polymer formula such as adding polyethylene or ethylene/vinyl acetate copolymer to polystyrenic-based foam systems to create interphase domains that cause cell wall rupture. By regulating the polymer system components and crystallization initiating temperature, open-cell content and microporous cell membrane uniformity can be controlled. Ethylene-styrene interpolymers can be added to alkenyl aromatic polymers to control open-cell quality and improve surface quality and processability. Small amounts of polystyrene-based polymers are sometimes added to polyolefin-based foams to increase open-cell content.

A plasticizing agent may also be added to enhance open-cell formation. A plasticizing agent is a chemical agent that imparts flexibility, stretchability and workability. The type of plasticizing agent has an influence on foam gel properties, blowing agent migration resistance, cellular structure, including the fine cell size, and number of open cells. Typically plasticizing agents are of low molecular weight. The increase in polymer chain mobility and free volume caused by incorporation of a plasticizing agent typically results in a Tg decrease, and plasticizing agent effectiveness is often characterized by this measurement. Petroleum-based oils, fatty acids, and esters are commonly used and act as external plasticizing agents or solvents because they do not chemically bond to the polymer yet remain intact in the polymer matrix upon crystallization.

The plasticizing agent increases cell connectivity by thinning membranes between cells to the point of creating porous connections between cells; thus, the plasticizing agent increases open-cell content. Suitably, the plasticizing agent is included in an amount between about 0.5% and about 10%, or between about 1% and about 10%, by weight, of the thermoplastic foam. The plasticizing agent is gradually and carefully metered in increasing concentration into the foam polymer formula during the foaming process because too much plasticizing agent added at once creates cellular instability, resulting in cellular collapse.

Examples of suitable plasticizing agents include polyethylene, ethylene vinyl acetate, mineral oil, palm oil, waxes, esters based on alcohols and organic acids, naphthalene oil, paraffin oil, and combinations thereof. A commercially available example of a suitable plasticizing agent is a small-chain polyethylene that is produced as a catalytic polymerization of ethylene; because of its low molecular weight it is often referred to as a "wax." This low-density, highly branched polyethylene "wax" is available from Eastman Chemical Company of Kingsport, Tenn., U.S.A., under the trade designation EPOLENE® C-10.

In order for the foam to be used in personal care and medical product applications and many absorbent wiping articles and non-personal care articles, the foam must meet stringent chemical and safety guidelines. A number of plasticizing agents are FDA-approved for use in packaging materials. These plasticizing agents include: acetyl tributyl citrate; acetyl triethyl citrate; p-tert-butylphenyl salicylate; butyl stearate; butylphthalyl butyl glycolate; dibutyl sebacate; di-(2-ethylhexyl) phthalate; diethyl phthalate; diisobutyl adipate; diisooctyl phthalate; diphenyl-2-ethylhexyl phosphate; epoxidized soybean oil; ethylphthalyl ethyl glycolate; glycerol monooleate; monoisopropyl citrate; mono-, di-, and tristearyl citrate; triacetin (glycerol triacetate); triethyl citrate; and 3-(2-xenoyl)-1,2-epoxypropane.

In certain embodiments, the same material used as the thermoplastic elastomer may also be used as the plasticizing agent. For example, the KRATON® styrene block copolymers, described above, may be used as the thermoplastic elastomer and a plasticizing agent.

Various additives such as lubricants, acid scavengers, stabilizers, colorants, adhesive promoters, fillers, smart-chemicals, foam regulators, various UV/infrared radiation stabilizing agents, antioxidants, flame retardants, smoke suppressants, anti-shrinking agents, thermal stabilizers, rubbers (including thermosets), anti-statics, permeability modifiers, and other processing and extrusion aids including mold release agents, and anti-blocking agents, and the like can also be included in the thermoplastic foam.

The ingredients of the thermoplastic foam may be heated and mixed together using conventional techniques, suitably at a temperature of about 100° C. to about 500° C., or high enough to melt the ingredients. The polymer melt can then be foamed using conventional techniques. For instance, the polymer melt can be continuously extruded to form the low density, flexible, resilient, absorbent open-cell thermoplastic foam. The open-cell content can be adjusted by varying the amounts of surfactant and (if used) plasticizer, or by varying the process conditions as explained above.

To produce thermoplastic foam for disposable personal care products, continuous plastic extrusion processes are typically utilized. Certain injection molding and batch processes can also be employed. Often tandem screw-type extruders are used because of the need for tight control of extrusion temperatures to produce open-cell foam. The first extruder typically contains several zones including: feed and conveying, compression, melting, metering and mixing zones. If one extruder is being used, a cooling zone is utilized prior to polymer melt discharge, foaming, and shaping. The first extruder is typically hopper loaded with resin and additives using dry/blend/metering equipment and/or having the additive(s) incorporated into the pelletized polymer concentrate such as in a masterbatch. The resins, additives, and/or masterbatch are then heated in the extruder to form a plasticized or melt polymer system, often with zoned temperature control using extruder cooling/heating systems.

Physical blowing agents are typically added after the melt temperature has been heated to a temperature at or above the highest polymer glass transition temperature or melting temperature to form a foamable melt. The inlet for a physical blowing agent is typically between the metering and mixing zones. The blowing agent is mixed thoroughly with the melted polymer at a sufficiently elevated pressure to prevent melt expansion. With a nucleating agent and blowing agent blended in the polymer melt, the foamable melt is typically cooled to a lower temperature to control the desired foam cell structure.

With tandem extruders, the cooling is performed in a second extruder which is connected downstream of the first extruder through a heated cross-over supply pipe. In single extruders, cooling is typically performed upstream of the discharge orifice. Often cooling/heating systems with process temperature control loops are incorporated to tightly control foam bubble nucleation/growth within the melt. The optimum cooling temperature is typically at or slightly above the glass transition temperature or melting point of the melt. The melt is then extruded through a die to a lower pressure (typically atmospheric or a vacuum) to cause thermodynamic instability and foaming which then cools and crystallizes the plastic to form foam and solidifies to form a web or product. Often circular, annular or slit dies, including curtain dies, and the like are used, often with a mandrel, to shape and draw the web to the desired gauge, shape and orientation with foam expansion and cooling.

Various equipment configurations using such extrusion can be used to manufacture thermoplastic expanded foam, extruded sheet, stranded foam, rod, pipe, block, plank, film, and beads. Foam laminates and composites can also be made with such equipment. Various specialized equipment can be employed upstream of specially designed dies to enhance mixing, cooling, cellular structure, metering, and foaming and include static mixers, gear pumps, and various extruder screw designs. Stretching equipment, including roller nips, tenters, and belts, is sometimes used immediately downstream of discharge to elongate cellular shape to enhance absorbency. Microwave irradiation for cross-linking, foaming activation, and use of mechanical means can also be used to enhance foam properties. Foam contouring, shaping (e.g. use of a wire mesh pattern) and the like, using thermoforming, and other such thermal processes can be used to control shaping and absorbent swelling.

Secondary post-treatment processes can be performed to further improve absorbency, fit, and similar properties including mechanical needling, stretching, brushing, scarfing, buffing/sanding, and drawing for controlling cellular orientation, aesthetics, and softening. Calendaring and creping can also be used to soften and rupture cell membranes to improve cellular connectivity, and thermoforming can be used to shape the foam absorbent. Often a foam surface skin may form during extrusion, which can later be skived or sliced off, needle-punched, brushed, scraped, buffed, scarved, sanded, or perforated to remove the barrier. Mechanical, hydraulic, thermal, or laser perforation can also be used to soften foam and further increase open-cell content.

Post-densification of the foam structure, after extrusion, can be employed to enhance functionality. The foam of the invention can be laminated to other layers, resulting in structures having various functionalities.

EXAMPLES

Thermoplastic foams were produced using blends of thermoplastic elastomer, ethylene ionomer, stiff polymer and surfactant as described below. All foams were produced using a 27-mm LEISTRITZ® co-rotating twin screw extruder, available from American Leistritz Extruder Corporation in Somerville, N.J., U.S.A., equipped for direct injection of carbon dioxide gas. The foam polymer formulas were heated to about 200 degrees Celsius in the extruder and subsequently foamed using carbon dioxide (added at 6%, by weight, of the foam polymer formula) as a blowing agent. Extrusion temperatures and pressures were adjusted for optimum foam expansion and open-cell connectivity. Each of the foam samples was tested for bulk density, buckling, pressure, open-cell content, fluid intake rating, and vertical wicking height, using the test procedures described below.

Example 1

Foam Samples 1A through 1E were extruded using a Leistritz 27 mm co-rotating twin screw extruder fitted with a gas injection system. Carbon dioxide was injected at a rate of approximately 2 parts per 100 parts of polymer. Each extrusion was carried out at a rate of 2 kg/hr and each foam was extruded through a die with three holes, each with a diameter of 2 mm. The extrusion temperature was adjusted for optimal foam properties. Foam composition and properties are shown in Table 1.

TABLE 1

| Composition | A | B | C | D | E |
|---|---|---|---|---|---|
| Class A: Elastomer (parts by weight) | Kraton G1657 SEBS (38.8) | Kraton G1657 SEBS (29.0) | Kraton G1657 SEBS (9.7) | Kraton D1119P SIS (29.1) | Kraton G1657 SEBS (29.2) |
| Class B: Ionomer (parts by weight) | None | DuPont Surlyn E-100672-126 (9.8) | DuPont Surlyn E-100672-126 (29.1) | DuPont Surlyn E-100672-126 (9.8) | DuPont Surlyn E-100672-126 (29.1) |
| Class C: Stiff Polymer (parts by weight) | Dow Styron 685D polystyrene (58.2) | Dow Styron 685D polystyrene (58.4) | Dow Styron 685D polystyrene (58.3) | Dow Styron 685D polystyrene (58.2) | Dow Styron 685D polystyrene (38.8) |
| Class D: Surfactant (parts by weight) | Clariant Hostastat HS-1 (3.0) | Clariant Hostastat HS-1 (2.8) | Clariant Hostastat HS-1 (2.9) | Clariant Hostastat HS-1 (2.9) | Clariant Hostastat HS-1 (2.9) |
| Other additives (parts by weight) | Luzenac Mistron Vapor talc (1.1) | Luzenac Mistron Vapor talc (1.0) | Luzenac Mistron Vapor talc (1.0) | Luzenac Mistron Vapor talc (1.0) | Luzenac Mistron Vapor talc (1.0) |
| Density (kg/m$^3$) | 195 | 201 | 218 | 139 | 179 |
| Buckling Pressure (kPa) | 602 | 644 | >684 | 384 | 221 |
| Open-cell (%) | 71 | 72 | 62 | 75 | 72 |
| Fluid Intake Rating | 7.3 | 9.0 | 8.0 | 9.0 | 6.7 |
| Vertical Wicking Height (cm) | 4.4 | 5.9 | 5.9 | 5.4 | 6.0 |

As shown above, Example 1E shows an embodiment of the invention resulting in improved wicking height and reduced buckling pressure compared to Examples 1A through 1D.

Example 2

The foams of Examples 2A through 2D were produced according to the process described for Example 1. The compositions and test results are indicated in Table 2.

TABLE 2

| Composition | A | B | C | D |
|---|---|---|---|---|
| Class A: Elastomer (parts by weight) | Kraton D1119P SIS (29.1) | Kraton G1657 SEBS (24.3) | Kraton G1657 SEBS (29.2) | Kraton G1657 SEBS (29.2) |
| Class B: Ionomer (parts by weight) | DuPont Surlyn E-100672-126 (29.1) | DuPont Surlyn E-100672-126 (48.5) | DuPont Surlyn E-100672-126 (38.8) | DuPont Surlyn E-100672-126 (29.1) |
| Class C: Stiff Polymer (parts by weight) | Dow Styron 685D polystyrene (38.8) | Dow Styron 685D polystyrene (24.3) | Dow Styron 685D polystyrene (29.1) | Dow Styron 685D polystyrene (38.8) |
| Class D: Surfactant (parts by weight) | Clariant Hostastat HS-1 (3.0) | Clariant Hostastat HS-1 (2.9) | Clariant Hostastat HS-1 (2.9) | Clariant Hostastat HS-1 (2.9) |
| Other additives (parts by weight) | Luzenac Mistron Vapor talc (1.1) | Luzenac Mistron Vapor talc (1.0) | Luzenac Mistron Vapor talc (1.0) | Luzenac Mistron Vapor talc (1.0) |
| Density (kg/m$^3$) | 119 | 117 | 123 | 179 |
| Buckling Pressure (kPa) | 52 | 79 | 113 | 221 |
| Open-cell (%) | 84 | 78 | 81 | 72 |
| Fluid Intake Rating | 8.3 | 5.0 | 4.3 | 6.7 |
| Vertical Wicking Height (cm) | 3.4 | 3.2 | 5.5 | 6.0 |

Compared to the foams of Example 1, the foams of Examples 2A through 2C had reduced density and buckling pressure with high open-cell content. Example 2D duplicated Example 1E. None of Examples 2A through 2C had a wicking height as high as the 6.0 cm value observed for Example 2D.

Example 3

The foams of Examples 3A and 3B were produced according to the process described for Example 1. Instead of using styrene as the stiff polymer, as in Examples 1 and 2, linear low density was employed in Example 3. Example 3A demonstrates the effects of eliminating the elastomer. As shown in Table 3, Example 3B (containing the elastomer) yields a foam having lower density, much lower buckling pressure, much higher open-cell content and much higher fluid intake rating.

TABLE 3

| Composition | A | B |
|---|---|---|
| Class A: Elastomer (parts by weight) | None | Kraton G1657 SEBS (24.3) |
| Class B: Ionomer (parts by weight) | DuPont Surlyn E-100672-126 (63.1) | DuPont Surlyn E-100672-126 (48.5) |
| Class C: Stiff Polymer (parts by weight) | Dow Dowlex 2036G LLDPE (34.0) | Dow Dowlex 2036G LLDPE (24.3) |
| Class D: Surfactant (parts by weight) | Clariant Hostastat HS-1 (2.9) | Clariant Hostastat HS-1 (2.9) |
| Other additives (parts by weight) | Luzenac Mistron Vapor talc (1.0) | Luzenac Mistron Vapor talc (1.0) |
| Density (kg/m$^3$) | 198 | 156 |
| Buckling Pressure (kPa) | 207 | 125 |
| Open-cell (%) | 37 | 77 |
| Fluid Intake Rating | 3.7 | 7.5 |
| Vertical Wicking Height (cm) | 2.0 | 1.9 |

Example 4

The foams of Examples 4A and 4B were produced according to the process described for Example 1. The compositions and test results are indicated in Table 4. The results indicate the effects of using a particular surfactant combination versus a single surfactant.

TABLE 4

| Composition | A | B |
|---|---|---|
| Class A: Elastomer (parts by weight) | Kraton D1119P SIS (29.1) | Kraton D1119P SIS (28.9) |
| Class B: Ionomer (parts by weight) | DuPont Surlyn E-100672-126 (29.1) | DuPont Surlyn E-100672-126 (28.9) |
| Class C: Stiff Polymer (parts by weight) | Dow Styron 685D polystyrene (38.8) | Dow Styron 685D polystyrene (38.7) |
| Class D: Surfactant (parts by weight) | Clariant Hostastat HS-1 (3.0) | Clariant Hostastat HS-1 (1.4) + BASF Masil SF-19 (1.0) |
| Other additives (parts by weight) | Luzenac Mistron Vapor talc (1.1) | Luzenac Mistron Vapor talc (1.1) |
| Density (kg/m$^3$) | 119 | 163 |
| Buckling Pressure (kPa) | 52 | 157 |
| Open-cell (%) | 84 | 74 |
| Fluid Intake Rating | 8.3 | 4.8 |
| Vertical Wicking Height (cm) | 3.4 | 4.4 |

As shown above, the foam of Example 4B has increased density and buckling pressure with reduced open-cell and fluid intake rating compared to Example 4A. The increase in buckling pressure is greater than is explained by the increase in density. The typically accepted relationship is that the ratio of the density squared is equal to the ratio of the buckling pressure. This is true if the cellular structure remains the same. The reduction in open-cell content would indicate a different cellular structure and help explain the change in buckling pressure. The reduced fluid intake rating would indicate that the cells are less wettable or that the connection between the cells is small. Both of these explanations should lead to a reduced wicking height. The increased wicking height of Example 4B further emphasizes a difference in cellular structure. Given this evidence, it is apparent that the surfactant is not just a wetting agent, but an integral part of the foaming process.

Example 5

The foams of Examples 5A and 5B were produced according to the process described for Example 1. The compositions and test results are indicated in Table 5. Example 5A demonstrates the effects of eliminating the ionomer from the thermoplastic foam.

TABLE 5

| Composition | A | B |
|---|---|---|
| Class A: Elastomer (parts by weight) | Kraton G1657 SEBS (67.1) | Kraton G1657 SEBS (57.7) |
| Class B: Ionomer (parts by weight) | None | DuPont Surlyn E-100672-126 (9.6) |
| Class C: Stiff Polymer (parts by weight) | Dow Styron 685D polystyrene (28.8) | Dow Styron 685D polystyrene (28.8) |
| Class D: Surfactant (parts by weight) | Clariant Hostastat HS-1 (3.1) | Clariant Hostastat HS-1 (2.9) |
| Other additives (parts by weight) | Luzenac Mistron Vapor talc (1.0) | Luzenac Mistron Vapor talc (1.0) |
| Density (kg/m$^3$) | 616 | 191 |
| Buckling Pressure (kPa) | 705 | 139 |
| Open-cell (%) | Not Tested | 80 |
| Fluid Intake Rating | Not Tested | 9.0 |
| Vertical Wicking Height (cm) | Not Tested | 4.0 |

Example 5A shows that a blend of Class A, C and D is not foamable to a low density. Open-cell and absorbent properties of Example 5A were not tested because it was not at a low enough density to be suitable as an absorbent article. Example 5B shows that the addition of a small amount of ethylene ionomer (Class B material) enables the foaming of this blend to a low density and enhanced all properties necessary for an absorbent article for personal hygiene.

Test Procedures

Foam Density

To determine foam density, the basis weight was first measured according to ASTM D1622-98. The thickness was measured using a hand micrometer without compressing the foam. The bulk density was then determined by dividing the basis weight by the thickness.

Buckling Pressure

The buckling (bending) pressure was determined by compression of the foam samples between two plates. Each foam sample, one inch in length by 0.2-0.4 inch in diameter, was placed and centered with the long dimension positioned perpendicular to the compression plates. The compression plates used consisted of an upper plate that was 2 inches in diameter and composed of Lexan® and a lower plate that was 6 inches in diameter and composed of steel. The plates were compressed at a constant rate of 5 mm/min. and the force to achieve this rate was recorded. The movement of the plates and the force measurements were performed using a Sintech 2 testing unit, Model 3108.129 manufactured by MTS Systems Corp., Eden Prairie, Minn. The force was divided by the cross-sectional area of the sample in contact with the compressing plates, yielding units of pressure. The pressure required to bend the sample, which appeared as the maximum pressure, was the buckling pressure.

Absorbency

Absorbency or saturated capacity is determined using a Saturated Capacity (SAT CAP) tester with a Magnahelic vacuum gage and a latex dam, comparable to the following description. Referring to FIGS. 1-3, a Saturated Capacity tester vacuum apparatus 110 comprises a vacuum chamber 112 supported on four leg members 114. The vacuum chamber 112 includes a front wall member 116, a rear wall member 118 and two side walls 120 and 121. The wall members are sufficiently thick to withstand the anticipated vacuum pressures, and are constructed and arranged to provide a chamber having outside dimensions measuring 23.5 inches in length, 14 inches in width and 8 inches in depth.

A vacuum pump (not shown) operably connects with the vacuum chamber 112 through an appropriate vacuum line conduit and a vacuum valve 124. In addition, a suitable air bleed line connects into the vacuum chamber 112 through an air bleed valve 126. A hanger assembly 128 is suitably mounted on the rear wall 118 and is configured with S-curved ends to provide a convenient resting place for supporting a latex dam sheet 130 in a convenient position away from the top of the vacuum apparatus 110. A suitable hanger assembly can be constructed from 0.25 inch diameter stainless steel rod. The latex dam sheet 130 is looped around a dowel member 132 to facilitate grasping and to allow a convenient movement and positioning of the latex dam sheet 130. In the illustrated position, the dowel member 132 is shown supported in a hanger assembly 128 to position the latex dam sheet 130 in an open position away from the top of the vacuum chamber 112.

A bottom edge of the latex dam sheet 130 is clamped against a rear edge support member 134 with suitable securing means, such as toggle clamps 140. The toggle clamps 140 are mounted on the rear wall member 118 with suitable spacers 141 which provide an appropriate orientation and alignment of the toggle clamps 140 for the desired operation. Three support shafts 142 are 0.75 inches in diameter and are removably mounted within the vacuum chamber 112 by means of support brackets 144. The support brackets 144 are generally equally spaced along the front wall member 116 and the rear wall member 118 and arranged in cooperating pairs. In addition, the support brackets 144 are constructed and arranged to suitably position the uppermost portions of the support shafts 142 flush with the top of the front, rear and side wall members of the vacuum chamber 112. Thus, the support shafts 142 are positioned substantially parallel with one another and are generally aligned with the side wall members 120 and 121. In addition to the rear edge support member 134, the vacuum apparatus 110 includes a front support member 136 and two side support members 138 and 139. Each side support member measures about 1 inch in width and about 1.25 inches in height. The lengths of the support members are constructed to suitably surround the periphery of the open top edges of the vacuum chamber 112, and are positioned to protrude above the top edges of the chamber wall members by a distance of about 0.5 inches.

A layer of egg crating type material 146 is positioned on top of the support shafts 142 and the top edges of the wall members of the vacuum chamber 112. The egg crate material extends over a generally rectangular area measuring 23.5 inches by 14 inches, and has a depth measurement of about 0.38 inches. The individual cells of the egg crating structure measure about 0.5 inch square, and the thin sheet material comprising the egg crating is composed of a suitable material, such as polystyrene. For example, the egg crating material can be McMaster Supply Catalog No. 162 4K 14, translucent diffuser panel material. A layer of 6 mm (0.25 inch) mesh TEFLON®-coated screening 148, available from Eagle Supply and Plastics, Inc., in Appleton, Wis., U.S.A., which measures 23.5 inches by 14 inches, is placed on top of the egg crating material 146.

A suitable drain line and a drain valve 150 connect to bottom plate member 119 of the vacuum chamber 112 to provide a convenient mechanism for draining liquids from the vacuum chamber 112. The various wall members and support members of vacuum apparatus 110 may be composed of a suitable noncorroding, moisture-resistant material, such as polycarbonate plastic. The various assembly joints may be affixed by solvent welding, and the finished assembly of the tester is constructed to be watertight. A vacuum gauge 152 operably connects through a conduit into the vacuum chamber 112. A suitable pressure gauge is a Magnahelic differential gauge capable of measuring a vacuum of 0-100 inches of water, such as a No. 2100 gauge available from Dwyer Instrument Incorporated in Michigan City, Ind., U.S.A.

The dry product or other absorbent structure is weighed and then placed in excess 0.9% NaCl saline solution and allowed to soak for twenty minutes. After the twenty minute soak time, the absorbent structure is placed on the egg crate material and mesh TEFLON@-coated screening of the Saturated Capacity tester vacuum apparatus 110. The latex dam sheet 130 is placed over the absorbent structure(s) and the entire egg crate grid so that the latex dam sheet 130 creates a seal when a vacuum is drawn on the vacuum apparatus 110. A vacuum of 0.5 pounds per square inch (psi) is held in the Saturated Capacity tester vacuum apparatus 110 for five minutes. The vacuum creates a pressure on the absorbent structure(s), causing drainage of some liquid. After five minutes at 0.5 psi vacuum, the latex dam sheet 130 is rolled back and the absorbent structure(s) are weighed to generate a wet weight.

The overall capacity of each absorbent structure is determined by subtracting the dry weight of each absorbent from the wet weight of that absorbent, determined at this point in the procedure. The 0.5 psi SAT CAP or SAT CAP of the absorbent structure is determined by the following formula:

SAT CAP=(wet weight−dry weight)/dry weight;

wherein the SAT CAP value has units of grams of fluid/gram absorbent. For both overall capacity and SAT CAP, a minimum of four specimens of each sample should be tested and the results averaged. If the absorbent structure has low integrity or disintegrates during the soak or transfer procedures, the absorbent structure can be wrapped in a containment material such as paper toweling, for example SCOTT® paper towels manufactured by Kimberly-Clark Corporation, Neenah, Wis., U.S.A. The absorbent structure can be tested with the overwrap in place and the capacity of the overwrap can be independently determined and subtracted from the wet weight of the total wrapped absorbent structure to obtain a wet absorbent weight.

Fluid Intake Rating

Foam saline fluid intake rating is measured by the following method. A foam specimen having a length in the machine direction of formation is cut to a 0.25 inch width and placed so that a cut edge is perpendicular to gravity. In other words, the sample is vertically disposed so that the cut edge defines an upper horizontal surface. The cut edge should have a surface area of at least 0.04 in$^2$. One droplet of 0.9% NaCl saline solution is placed onto the cut edge. The droplet has a mass of 0.038-0.041 grams, and may be delivered using a suitable pipette or other instrument. If the droplet is immediately absorbed, the intake rating of 9 is given to the specimen. If the droplet is absorbed within a second but is slow enough that a meniscus is formed on the surface, the intake rating for the specimen is assigned a value of 5. If the droplet is absorbed within five seconds, the fluid intake rating of the specimen is 3. If a substantial amount of fluid is absorbed into the foam but the droplet is not completely absorbed within five seconds, the specimen intake rating is assigned a value of 1. The specimen intake rating is zero if little or none of the droplet is absorbed by the foam within five seconds. The reported rating is the average of at least twelve tested specimens. A fluid intake rating of 5 or greater is desirable for use in high-flow absorbent applications such as diapers.

Vertical Wicking Test Method

A sample of foam is cut and mounted so that it hangs in a vertical orientation to gravity with an exposed foam edge in a substantially horizontal orientation. A sufficiently large reservoir of 0.9% NaCl saline test solution is raised, using a standard lab jack, so that the foam's horizontal edge extends approximately two millimeters beneath the surface of the saline. A timer is started simultaneously to the penetration of the foam into the saline. After fifteen minutes, the height of the fluid in the foam is measured relative to the surface of the saline. If desired, the saline can contain a non-surface active, non-chromatographic dye to aid in identifying the penetration and wicking of the test fluid within the foam. Alternatively, the foam may be marked at the surface of the fluid and the fluid reservoir lowered to remove further contact with the foam. To compensate for possible foam expansion upon hydration, the foam may be marked at the fluid surface after the wicking time. Measurement of the fluid height in the foam using the initial foam dimensions may be done via appropriate means including x-ray imaging, optical measurement, or slicing sections of the foam until 0.9% NaCl saline test solution is apparent in the slice.

While the embodiments of the invention disclosed herein are presently preferred, various modifications and improvements can be made without departing from the spirit and scope of the invention. The scope of the invention is indicated by the appended claims, and all changes that fall within the meaning and range of equivalents are intended to be embraced therein.

We claim:

1. An open-cell, absorbent thermoplastic foam, including at least 75% by weight of a foam formula mixture which comprises:
    A) about 5 to about 70 parts by weight of a thermoplastic styrene block copolymer elastomer;
    B) about 5 to about 70 parts by weight of an ethylene ionomer;
    C) about 15 to about 60 parts by weight of a stiff polymer selected from the group consisting of polystyrene, high impact polystyrene, and combinations thereof; and
    D) about 0.5 to about 5 parts by weight of a surfactant selected from the group consisting of ethoxylated dimethylsilicone surfactants, polyoxyethylene copolymer surfactants, block copolymers of ethylene oxide and propylene oxide, organic sulfonates, alkylpolyglycosides, polyolefin glycol derivatives, and combinations thereof;
    wherein the thermoplastic foam has an open-cell content of at least about 70% and a vertical wicking height of at least about 4.5 cm.

2. The thermoplastic foam of claim 1, wherein the thermoplastic styrene block copolymer elastomer comprises a styrene block copolymer elastomer selected from the group consisting of styrene diblock copolymers, styrene triblock copolymers, styrene tetrablock copolymers and combinations thereof.

3. The thermoplastic foam of claim 1, wherein the ethylene ionomer comprises a thermoplastic ionomer having the following formula:

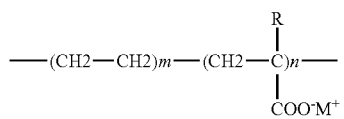

where M is sodium, potassium, lithium, magnesium, zinc or strontium,
    R is hydrogen or an alkyl group having 1 to 6 carbon atoms,
    m and n are integers, and
    the ratio of m/n is about 10 to about 100.

4. The thermoplastic foam of claim 1, where the ionomer has a percent neutralization of about 5% to about 100%.

5. The thermoplastic foam of claim 1, wherein the ionomer has a percent neutralization of about 8% to about 85%.

6. The thermoplastic foam of claim 1, wherein the surfactant comprises a compound selected from the group consisting of ethoxylated dimethylsiloxanes.

7. The thermoplastic foam of claim 1, wherein the surfactant comprises a compound selected from the group consisting of polyoxyethylene sorbitan monopalmitate, polyoxyethylene sorbitan monostearate, and combinations thereof.

8. The thermoplastic foam of claim 1, wherein the surfactant comprises a compound selected from the group consisting of alkyl sulfonates, aryl sulfonates, alkylaryl sulfonates, ether sulfonates, and combinations thereof.

9. The thermoplastic foam of claim 1, wherein the surfactant comprises an alkyl sulfonate.

10. The thermoplastic foam of claim 1, wherein the surfactant comprises an alkyl polyglycoside.

11. An absorbent article comprising the thermoplastic foam of claim 1.

12. A low density, open-cell, absorbent thermoplastic foam, including at least 75% by weight of a foam formula mixture which comprises:
    A) 10 to about 50 parts by weight thermoplastic styrene block copolymer elastomer;
    B) 10 to about 50 parts by weight ethylene ionomer;
    C) about 25 to about 60 parts by weight stiff polymer selected from the group consisting of polystyrene, high impact polystyrene, and combinations thereof; and
    D) about 0.5 to about 5 parts by weight of a surfactant selected from the group consisting of ethoxylated dimethylsilicone surfactants, polyoxyethylene copolymer surfactants, block copolymers of ethylene oxide and propylene oxide, organic sulfonates, alkylpolyglycosides, polyolefin glycol derivatives, and combinations thereof;
    wherein the thermoplastic foam has a density of about 60 kg/m$^3$ to about 160 kg/m$^3$, a vertical wicking height of at least about 4.5 cm, and an open-cell content of at least about 70%.

13. The thermoplastic foam of claim 12, wherein the foam formula mixture comprises:
    A) about 20 to about 40 parts by weight of the thermoplastic styrene block copolymer elastomer;
    B) about 15 to about 40 parts by weight of the ethylene ionomer;
    C) about 35 to about 60 parts by weight of the stiff polymer; and
    D) about 2 to about 4 parts by weight of the surfactant.

14. The thermoplastic foam of claim 12, wherein the ethylene ionomer comprises a partially neutralized polymer selected from the group consisting of partially neutralized ethylene acrylic acid, partially neutralized ethylene alkyl acrylic acids, partially neutralized ethylene alkyl acrylates, and combinations thereof.

15. The thermoplastic foam of claim 12, wherein the surfactant comprises an alkyl sulfonate.

16. The thermoplastic foam of claim 12, wherein the thermoplastic styrene block copolymer elastomer is selected from the group consisting of styrene diblock copolymers, styrene triblock copolymers, styrene tetrablock copolymers and combinations thereof.

17. The thermoplastic foam of claim 12, wherein the foam has a density of about 125 kg/m$^3$ or less.

18. The thermoplastic foam of claim 12, wherein the foam has a buckling pressure of about 250 kPa or less.

19. The thermoplastic foam of claim 18, wherein the buckling pressure is about 100 kPa or less.

20. The thermoplastic foam of claim 12, wherein the foam has a fluid intake rating of about 5 to 9.

21. The thermoplastic foam of claim 20, wherein the fluid intake rating is about 7 to 9.

22. An absorbent article comprising the thermoplastic foam of claim 12.

23. A low density, open-cell thermoplastic foam including at least 75% by weight of a foam formula mixture, the foam formula mixture comprising:
   A) about 5 to about 70 parts by weight of a thermoplastic elastomer selected from the group consisting of styrene block copolymer elastomers and combinations thereof;
   B) about 5 to about 70 parts by weight of an ethylene ionomer;
   C) about 15 to about 60 parts by weight of a stiff polymer selected from the group consisting of polystyrene, high impact polystyrene, and combinations thereof; and
   D) about 0.5 to about 5 parts by weight of a surfactant selected from the group consisting of ethoxylated dimethylsilicone surfactants, polyoxyethylene copolymer surfactants, block copolymers of ethylene oxide and propylene oxide, organic sulfonates, alkylpolyglycosides, polyolefin glycol derivatives, and combinations thereof;
   wherein the thermoplastic foam has a fluid intake rating of about 5 to 9, a density of about 125 kg/m$^3$ or less, and an open-cell content of at least about 70%.

24. An absorbent article comprising the thermoplastic foam of claim 23.

* * * * *